United States Patent [19]

Matsuo et al.

[11] Patent Number: 4,472,503

[45] Date of Patent: Sep. 18, 1984

[54] METHOD FOR ENZYMATIC TRANSESTERIFICATION OF LIPID AND ENZYME USED THEREIN

[75] Inventors: Takaharu Matsuo; Norio Sawamura, both of Sennan; Yukio Hashimoto, Kishiwada; Wataru Hashida, Osaka, all of Japan

[73] Assignee: Fuji Oil Company, Limited, Osaka, Japan

[21] Appl. No.: 492,003

[22] Filed: May 5, 1983

Related U.S. Application Data

[62] Division of Ser. No. 241,845, Mar. 9, 1981, Pat. No. 4,416,991.

[30] Foreign Application Priority Data

Mar. 8, 1980 [JP] Japan ............................. 55-29707
Mar. 8, 1980 [JP] Japan ............................. 55-29708

[51] Int. Cl.³ ............................................. C12N 11/14
[52] U.S. Cl. ................................. 435/176; 435/179; 435/180; 435/188; 435/198
[58] Field of Search .................. 426/33; 435/176, 188, 435/179, 180, 198

[56] References Cited

U.S. PATENT DOCUMENTS

| 3,498,882 | 3/1970 | Rogols et al. ................ 435/176 X |
| 3,519,538 | 7/1970 | Messing et al. ................ 435/176 |
| 3,666,627 | 5/1972 | Messing ........................ 435/176 |
| 4,258,133 | 3/1981 | Mirabel et al. ................. 435/176 |
| 4,268,527 | 5/1981 | Matsuo et al. ................. 426/33 |
| 4,275,081 | 6/1981 | Coleman et al. ............... 426/33 |

Primary Examiner—Robert A. Yoncoskie
Attorney, Agent, or Firm—Wenderoth, Lind & Ponack

[57] ABSTRACT

A method for the enzymatic transesterification useful for modification of a lipid which comprises continuously or repeatedly contacting an enzyme or an enzyme preparation having transesterification activities with a fresh supply of a dried fatty ester substrate such as fats and oils of glycerides. The enzyme or the enzyme preparation has transesterification activities (Kr value) of 0.01 or more as well as lipolytic activities. The enzyme preparation is prepared by dispersing, adsorbing or bonding an enzyme having lipolytic activities in or to a carrier and drying the resulting mixture at an adequately slow initial drying rate to activate or increase transesterification activities of the enzyme.

11 Claims, No Drawings

METHOD FOR ENZYMATIC TRANSESTERIFICATION OF LIPID AND ENZYME USED THEREIN

This is a division of application Ser. No. 241,845 filed Mar. 9, 1981, now U.S. Pat. No. 4,416,991.

The present invention relates to a method for the enzymatic transesterification of a lipid and an enzyme used therein.

As one of the methods for modifying a lipid, there has been employed a transesterification reaction, for example, between fatty acid residues in a lipid and other fatty acid residues in a reaction system. In the transesterification of a lipid, it has been known to use a metallic catalyst such as an alkaline metal, an alcoholate of an alkaline metal, an alkaline metal hydroxide or the like. However, when this transesterification is carried out in the presence of water, a free fatty acid, a peroxide or the like, the catalyst is deactivated. For example, it is reported that, when a fat or oil is treated by this transesterification, sodium methoxide used as the catalyst is deactivated at the rate of 0.3 part for each 0.1 part increase in water content and 0.1 part for each 0.1 increase in acid value (AV) [Journal of the American Oil Chemist's Society, 55, 796–804 (1978)]. Therefore, a fat or oil to be treated by this transesterification is thoroughly deacidified and dried before addition of such metallic catalyst and moisture content of the dried fat or oil to be treated is usually of the order of 0.01 %.

It has also been proposed to use a lipolytic enzyme in the transesterification of a lipid (e.g. Japanese Kokai Nos. 15687/1976 and 104506/1977). Since a selective transesterification reaction which has not been expected in the transesterification using a metallic catalyst can be effected by utilizing the specificity of a lipolytic enzyme, it is possible to modify a glyceride in the desired configuration and characteristics just as one wishes, that is, to obtain a so-called "tailor-made" glyceride by the transesterification using a lipolytic enzyme. In this enzymatic transesterification, unlike the above metallic catalyst, a lipid-degrading enzyme is not inactivated by water. On the contrary, it has generally been considered that the presence of water is essential for enzymatic reaction using various enzymes including the lipolytic enzyme, and an optimum pH thereof is also taken into consideration. Further, it is said that a lipolytic enzyme acts at interface in a heterogeneous system, one side of which is water. Therefore, almost all of the conventional processes of the enzymatic transesterification are carried out with the addition of water or without the drying of the reaction system.

However, another problem which has not been encountered in the transesterification using a metallic catalyst arises in the enzymatic transesterification. That is, since hydrolysis is unavoidable in the enzymatic transesterification, a free fatty acid (FFA) and other hydrolyzates such as a monoglyceride (MG) or a diglyceride (DG) are formed and hence, the yield of the desired esters such as a triglyceride (TG) is lowered and quality thereof is deteriorated because of difficulty of removing the hydrolyzates from the reaction mixture.

For example, in case of the preparation of TG, it is difficult to remove DG which is the most hardly removable among the hydrolyzates. Although, MG and FFA as well as DG form an eutectic mixture with TG and hinder the formation of crystal nuclei, MG and FFA contents in a reaction mixture can be considerably decreased by alkali refining and distillation. To the contrary, any effective industrial process for removing DG has not yet been established. K. G. Berger proves that, when palm oil contains 13 % of DG, the ratio of the solid fat to the total oil at 21° C. becomes as low as 80 % of that containing no DG and when the DG content becomes higher, it takes a longer time to transform the crystal form from $\alpha$-form into $\beta'$-form and further into $\beta$-form [Oil Palm News, 22, 10–18 (1977)]. The presence of DG hinders the formation of crystal nuclei and hence, difficulties arise in a fractionation operation at a low temperature, a tempering step in chocolate production or the like. Generally, it is desirable to minimize DG content in a fat or oil. At most about 12 %, particularly, in case of producing a cacao butter substitute, 6.5 % or less of DG content is preferable.

Further, although a lipolytic enzyme has been employed in various uses such as digestives, enzymatic flavors, tanning agents, detergents, cosmetics, brewing, stractural analysis of glycerides or the like, the worth of the enzyme is usually evaluated by the lipolytic activities(assay of the freed fatty acid)thereof, which is used as a measure in the preparation of an enzyme. In the conventional enzymatic transesterification, wherein lipolytic activities are also used as an important measure, as mentioned above, it has been considered that the enzymatic transesterification requires water, that is, the transesterification occurs as a result of a reversible reaction which involves both reactions of hydrolysis and synthesis and the hydrolysis is required for the enzymatic transesterification.

However, as a result of the present inventors' intensive study, it has been found that the lipolytic activities of an enzyme do not correspond to the transesterification activities thereof. For example, some lipolytic enzymes show inferior transesterification activities in a system having a low water content, while they have good lipolytic activities, and further, when several enzyme preparations are prepared from enzymes in the same lot having transesterification activities, they sometimes show different transesterification activities from one another even if they have similar lipolytic activities.

Under these circumstances, it is required to carry out the enzymatic transesterification in a reaction mixture having a low water content such as 0.18 % or less in order to obtain a lipid in high quality and hence, it is required to study transesterification activities of a lipolytic enzyme in order to obtain an enzyme preparation being stable and having high transesterification activities even if it is carried out in a reaction mixture having a low water content.

The present inventors have surprisingly found that an enzyme preparation having transesterification activities is increased in effectiveness by continuously or repeatedly using the preparation in a dried reaction system, that is, the formation of DG and other hydrolyzates is reduced and that an enzyme preparation having high transesterification activities, which have not been attained by a conventional enzyme preparation can be obtained.

One object of the present invention is to provide a method for the enzymatic transesterification useful for the modification of a lipid which comprises continuously or repeatedly contacting an enzyme preparation having transesterification activities with a fresh supply of a dried fatty ester substrate such as a triglyceride. Another object of the present invention is to provide an enzyme preparation useful for the enzymatic transesterification of a lipid having high transesterification activities which have not been attained by a conventional enzyme preparation. Still another object of the present invention is to provide a method for preparing the enzyme preparation which comprises dispersing, adsorbing or bonding an enzyme having lipid-degrading activities in or to a carrier in an aqueous system and drying the resulting mixture at an adequately slow initial rate of drying to activate or increase the transesterification activities of the enzyme.

These objects as well as other objects and advantages of the present invention will become apparent to those skilled in the art from the following description.

Firstly, the conception and definition of the term "transesterification activities" are explained.

In general, when a degree of conversion and a reaction time are represented by the symbols "x" and "t (day)", respectively, and a reaction rate (dx/dt) is proportional to $(1-x)$ wherein $x=1$ means a completely reacted state and $x=0$ means an unreacted state, the proportionality factor k is shown by the formula:

$$k = \frac{1}{t} \ln \frac{1}{1-x}$$

The degree of conversion of the transesterification is determined by selecting a suitable guide fatty acid and measuring the distributional change thereof which occurs in a dry reaction system. The term "completely reacted state" used herein means the state in which a constant distribution of a guide fatty acid has been substantially attained by a reaction for a sufficient time. However, when the enzyme to be used apparently has a certain specificity, it is convenient and there is no hindrance such as to assume that a theoretical "completely reacted state" exists. For example, when the transesterification is carried out by using a lipase which has specificity toward the 1-and 3-positions of a glyceride (which does not substantially act on the 2-position thereof), the state in which fatty acids at the 1- and 3-position of the glyceride are completely distributed at random and can be considered to be a "completely reacted state". The "transesterification activities" (absolute value) is expressed by the symbol "Ka" which is the product of the proportionality factor k and the value of "the amount of the substrate used/the amount of the enzyme used". The "transesterification activities" (relative value) is expressed by the symbol "Kr" which is determined by dividing Ka by lipolytic activities of 1 g of the enzyme used.

The following illustrates the definition of the "transesterification activities" of the present invention and the determination thereof in more detail.

A dry mixture of equivalent weight amounts of coconut oil (according to Japanese Pharmacopeia Standard) and methyl stearate (containing $C_{15}H_{31}COOCH_3$ and being substantially free from $C_{11}H_{23}COOCH_3$) (20 g, water content of the mixture being 0.02 wt. % or less) and an enzyme preparation, for example, a lipase preparation (1 g, moisture being removed as much as possible by vacuum drying) (total moisture content of the system being within the range of 0.08±0.02 %) are place in a 300 ml Erlenmyer flask with stopper. After replacing air in the flask with $N_2$, the reaction is carried out with stirring at 300 to 500 r.p.m. at 40° C. for 24 hours (1 day). A sample (20 mg) of the resulting reaction mixture is collected and subjected to thin layer chromatography. The fraction containing fatty acid methyl esters is collected and subjected to gas chromatography to determine the fatty acid composition in the fraction. Lauric acid derived from coconut oil is regarded as the guide fatty acid and the ratios of the guide fatty acid to the total fatty acids in the fraction at completely reacted stage, $t=1$ (day) and $t=0$ are determined. When the ratios at completely reacted state, at $t=1$ and at $t=0$ are represented by the symbols "a", "b" and "c", respectively, x, k and Ka are as follows:

$$x = \frac{b}{a}, k = \ln \frac{a}{a-b}, Ka = 20 \ln \frac{a}{a-b}.$$

When the lipase used has specificity toward the 1- and 3-positions of a glyceride, the symbol "a" can be determined by calculating the weight ratio of lauric acid residue bonded to the 1- and 3-positions of the glyceride in coconut oil to the sum of the amounts of total fatty acid residues bonded the 1- and 3-positions of the glyceride and the fatty acid residues in methyl stearate. When the enzyme used does not show any substantial selectivity toward any certain position of the glyceride, the "a" can be determined by calculating the weight ratio of the total lauric acid residue bonded to the glyceride to the sum of the amount of total fatty acid residues bonded to the glyceride and the fatty acid residues in the methyl ester.

The lipolytic activities can be expressed by the amount ($\mu$ M) of fatty acids formed per 1 minute by 1 g of an enzyme used and is determined according to the method described in Fukumoto et al, J. Gen. Appl. Microbiol., 9, 353 (1963). The adequency of the above definition is evaluated in Example 9 hereinafter.

Any enzyme or enzyme preparation which shows a certain transesterification activities in a dry reaction system and is capable of using repeatedly can be employed in the present invention. The method for preparing the enzyme preparation is not critical. Apparently, it is desirable that the Ka value of the enzyme or the enzyme preparation is higher and stability thereof is higher (i.e. activities are hardly lowered even being kept for a long period of time). Preferably, the enzyme or the enzyme preparation used in the present invention a Ka value of 5 or more.

However according to the present inventors' test of commercially available enzymes, it has been found that enzymes other than cell-bound enzymes (exocellular enzymes) hardly show the desired transesterification activities in a system having a low water content, and further that in the case of enzymes having little transesterification activities, it is necessary to subjected them to dispersion, adsorption, or bonding in or to a carrier in an aqueous system, followed by drying the resulting mixture at an adequately slow initial drying rate. That is, even if an enzyme itself does not show transesterification activities or the activities thereof is insufficient, as far as the enzyme has lipolytic activities, the enzyme is modified and improved in terms of the transesterification activities in a dry reaction system by the above treatment.

Thus, in the method for preparing the enzyme preparation of the present invention, an enzyme or an enzyme-containing material, such as microbial cells homogenates or extender containing material, having lipolytic activities, is used as the raw material. As far as the raw material has lipolytic activities, transesterification activities thereof can be activated, even if the raw material itself does not show the activities, but if it has no lipolytic activities, transesterification activities can not be activated by any treatment. Further, even if the drying rate is too fast to activate or increase transesterification activities as mentioned below, as far as the dried material maintains the lipolytic activities, according to the remaining activities, transesterification activities can be activated or increased by again hydrating the dried material and drying at a slow rate. Therefore, it is understood that the transesterification reaction requires a lipolytic active site. According to the present inventors' test of commercially available enzymes, certain kinds of cell-bound enzymes show a little transesterification activity, though they are not strong enough. However, the other lipolytic enzymes tested themselves hardly show transesterification activities. The origin, degree of purity and selectivity of the enzyme to be used are not critical and a wide variety of lipolytic enzymes such as those originated from microbe, molds, yeasts and, furthermore, tissues of higher animals and plants can be used. Examples of lipolytic enzymes used in the method for preparing the enzyme preparation of the present invention are those originated from microbes such as *Pseudomonas fluorescens, Thermomyces ibadanensis, Fumicorra ranuginosa* or the like; molds such as *Rhizopus delemar, Rhizopus japonicus* (cell-bound enzyme), *Rhizopus niveus, Asperigillus nigar, Mucor javanicus, Rhizopus arrhizus* (cell-bound enzyme) or the like; and yeasts such as *Candida cylindracae, Geotricum candidum* or the like; pancreas lipase; and rice bran lipase.

In order to utilize the advantages of the enzymatic transesterification and from a practical viewpoint, it is preferably to use an enzyme having a certain selectivity such as that toward specific positions of a glyceride or toward a specific kind of fatty acids.

It is necessary to disperse, adsorb or bond the enzyme or the enzyme-containing material having lipid-degrading activities in or to a carrier in an aqueous system. When the enzyme or the material is merely admixed with a carrier in a dry state, transesterification activities can not be activated or increased. Although the term "in an aqueous system" means that the system contains enough water to hydrate the protein of the enzyme, in order to shorten the time of the subsequent drying step, it is preferable to minimize the amount of water so as be not much excess over the water retention capacity of the enzyme and the carrier. The suitable carrier to be used is that having high water retention capacity and low adsorptivity such as diatomaceous earth, kaolinite, pearlite, silica gel, cellulose powder, polyvinyl alcohol, calcium carbonate or the like. When a carrier having high adsorptivity such as activated carbon, alumina or the like is used, the resulting transesterification activities are insufficient. This may be caused by blocking of an active site of the transesterification reaction. When a carrier having low or no water retention capacity, such as glass powder or the like is used, it is difficult to activate or increase the transesterification activities, since a large amount of carrier is needed so as to hydrate the carrier with an enzyme solution and the enzyme is insufficiently distributed on the carrier. The carrier may be in the form of powder, fibers or the like. However, it is preferable that the carrier be in the form of granules in view of the continuous use of the resulting enzyme preparation. In order to disperse, adsorb or bond the enzyme or the enzyme-containing material in or to the carrier, for example, the enzyme or the material is dissolved in water and then the resulting solution is admixed with the carrier, or the enzyme or the material is admixed with the carrier and then the resulting mixture is wetted by spraying water or contacting it with water vapor at a low temperature. The mixture ratio of the enzyme or the enzyme-containing material to the carrier varies according to water retention capacity of the carrier, but about 2:1 to 1:20 is preferable.

After the enzyme or the enzyme-containing material is dispersed, adsorbed or bonded in or to the carrier in an aqueous system, the resulting mixture is dried. In this drying step, even if the mixture is merely dried as fast as possible at such a rate that the enzyme maintains its lipolytic activities, the transesterification activities can not be activated or increased. That is, in order to activate or increase the above-mentioned $K_a$ or $K_r$, value, it is necessary to slow down the drying rate in the initial stage of the drying, that is, until water is removed to some extent from the starting hydrated mixture. The "slow initial drying rate" and the "period of the initial stage" being required to sufficiently increases the $K_a$ or $K_r$ values vary according to the components, other than enzyme in the starting mixture, the kind and nature of the carrier used, the relation between the apparatus to be used in the treatment and the amount of the mixture to be treated or the like, and they can not determined uniformly. However, they can be experimentally determined as follows:

Firstly, several runs are carried out with a varying drying rate and a suitable "slow drying rate" is determined by measuring the $K_r$ value of each run. Secondly, several runs are again carried out by, initially, drying at a the slow drying rate thus determined with varying period of time and, in the course of drying at a faster drying rate. The suitable "initial stage" is the period after which the change of the drying rate no longer affects the $K_r$ value of the resulting enzyme preparation.

Usually, the initial stage is over before the starting mixture reaches 0.4 of degree of moisture (ratio of the amount of water in the mixture to the dry weight of the mixture by taking the latter as 1). The slow drying rate mostly depends on the nature of the carrier used. Generally, in the case of using a carrier in the form of a powder having a high water retention capacity, the rate is such that the decrease in the degree of moisture is at most 0.3 per hour. In the case of using a carrier in the form of granules having a diameter of about 2 mm and having high water retention capacity, the rate is such that the decrease in the degree of moisture is at most 0.25 per hour, and more generally, a decrease of 0.1 or less per hour is preferable.

The drying can be carried out by various methods in which the controlled slow drying rate can be effected including vacuum drying, pneumatical drying and high-frequency radiation vacuum drying. However, under the conditions of freezing water in the mixture such as in freeze-drying, the transesterification activities can not be fully activated, while the lipid-degrading activities are maintained. This may be caused by the rapid solidification of water in the mixture. During the drying, if necessary, heating can be effected, but it is preferable to maintain the temperature at 50° C. or below at the initial stage of the drying. Dryness depends upon the particular use of the resulting enzyme preparation but, in order to use the preparation in a reaction system having a low water content such as 0.18% or less, it is preferable to dry the mixture of the enzyme or the enzyme-containing material until it contains a water content of 2%.

Thus, according to the method for preparing the enzyme preparation of the present invention, even if an enzyme does not show transesterification activities in a reaction system having a low water content, the activities can be activated or even if the activities thereof is weak, the intrinsic activities an be increased and hence, an enzyme preparation having high transesterfication activities, which has not been attained by a conventional enzyme preparation, can be obtained.

The results obtained from the present inventors' test of commercial available enzymes are as follows:

The Ka and Kr values of the commercially available lipases obtained were determined without any treatment of the enzymes. The Ka and Kr values thereof are shown in Table 1.

TABLE 1

| Origin of lipases | Ka | Kr × 10³ |
|---|---|---|
| Rhizopus niveus (product of A Co.) | 0.0 | 0.00 |
| Rhizopus japonicus | 12.0 | 7.5 |
| Aspergillus nigar | 0.0 | 0.00 |
| Mucor javanicus | 0.9 | 0.09 |
| Swine pancreas lipase | 2.3 | 0.47 |
| Rhizopus niveus (product of B Co.) | 0.2 | 0.01 |
| Candida cylindracae | 0.0 | 0.00 |
| Rhizopus delemar (product of C Co.) | 0.0 | 0.00 |
| Rhizopus delemar (procuct of D Co.) | 0.0 | 0.00 |

Although it is preferable to use an enzyme or an enzyme preparation having a Ka value of 5 or more in the present invention, as shown in Table 1, there is no lipase having a Kr value of 0.01 or more in the commercially available lipases tested. Further, these lipases were treated by dispersing, adsorbing or bonding them in or to a carrier in an aqueous system and drying rapidly or freeze-drying without inactivation of their activiites, but a 0.005 increase or more in the Kr value was not observed (see Reference Examples 2, 3 and 6 hereinafter).

In the enzymatic transesterification of the present invention, the cell-bound enzyme or the enzyme preparation having transesterification activities can be used and it is preferable to dry it as dry as possible. However, the enzyme or the enzyme preparation may contain at most about 4 to 5% of water since, in general, it is difficult to completely remove water therein without inactivation of its activities. In the present invention, the water content of the enzyme or the enzyme preparation is decreased by continuous or repeated use thereof. This decrease in water content of the enzyme or the enzyme preparation by continuous or repeated use together with use of a dried substrate containing a fatty ester controls formation of DG and the other hydrolyzates.

The fatty ester substrate used in the present invention should be dried to such dryness that at least the water content of the enzyme or the enzyme preparation to be used is not increased by the water in the substrate. Preferably, the total amount of water, including that in the enzyme or the enzyme preparation, and that in the substrate continuously or repeatedly supplied to the reaction system, should be maintained at a solubility limit of water in the fatty ester used or below. For example, when a fatty ester substrate is a fat or oil of glycerides, the fat or oil is preferably dried in such degree that the water content thereof becomes 0.18% or less. Even if the fat or oil contains no DG, though fats and oils generally contain a small amount of DG, hydrolyzates, particularly, about 6.5% of DG are formed in a transesterified product when water content of the fat or oil is more than 0.18%. For example, in many cases, palm oil without fractionation contains 6 to 8% of DG. If DG content is increased as much as 6.5% by a transesterification, the total DG content of such the palm oil becomes more than 12% after the transesterification and the resulting oil is hardly used in such fats and oils processing that crystal characteristics are closely related to the quality of products. It has been found that, when a fat or oil is a substrate to be continuously or repeatedly treated and moisture content (%) and DG content (%) thereof are represented by the symbols "w" and "y", respectively, it is desirable to decrease the value of y+34 w, preferably, to less than 12, more preferably, to less than 6.5. However, since the water content in the substrate to be treated becomes smaller, it becomes more difficult to dry, desired quality of products and ecomony of drying should be taken into consideration in order to determine to what extent below solubility limit of water in the substrate drying is effected. Generally, it is sufficient to dry the substrate used in the present invention to such degree as a stock oil used in a conventional transesterification using an alkaline metal catalyst which is elaborately dehydrated and dried (about 0.01% of water content).

As far as the substrate to be used is not deteriorated, any drying process including vacuum drying, vacuum heat drying and treatment with a dehydrating agent can be employed. In some cases, the transesterification may be carried out under a reduced pressure to remove water in the substrate or a dehydrating agent may be added to a reaction system during the transesterification. Examples of a dehydrating agent are zeolite, activated alumina, silica gel, anhydrous salts (e.g. anhydrous calcium carbonate, anhydrous sodium sulfate, etc.), ion exchange resins or the like.

Typical examples of the fatty ester substrate used in the present invention is a mixture of fats and oils of glycerides (e.g. animal fats and oils, vegetable fats and oils or microbial fats and oils, hydrogenated or fractionated fats and oils thereof) or a mixture of fats and oils of glycerides and $C_1$-$C_6$ lower alcohol esters of fatty acids havin $C_{10}$ to $C_{22}$ carbon atoms. Further, the substrate include other fatty esters, on which a lipolytic enzyme can act, such as propylene glycol ester, phospholipids (e.g. phosphatidyl choline, phosphatidyl ethanolamine, lecithin etc.), cholesterol esters, terpene alcohol esters (e.g. geranyol esters, farnesol esters etc.) or the like. Fatty acids having $C_3$ to $C_{22}$ carbon atoms may be present in the substrate together with these fatty esters. Besides, the substrate should be a liquid at a reaction temperature and, when a material, such as a saturated higher fatty acid having a melting point higher than the selected reaction temperature is used, the material may be dissolved in an inert organic solvent such as n-hexane. However, it is preferable to use the material as a lower alcohol ester thereof since a convenient apparatus and a convenient operation can be employed.

Particularly, in the production of a cacao butter substitute, it is desirable to obtain fats and oils of glycerides which comprise predominantly 1-palmityl-2-oleyl-3-stearyl glyceride, 1,3-distearyl-2-oleyl glyceride or mixtures thereof. In such case it is preferable to use a mixture of a fat or oil of glycerides containing a lot of oleic acid residue at 2-position, for example, olive oil, oleic safflower oil, palm oil, shea butter, sal fat (Shorea Robusta), mango fat, tea seed oil, camellia oil, a fractionated fat thereof, triolein or the like and a higher fatty acid or a lower alcohol esters thereof such as palmitic acid, stearic acid, or the like as the substrate and to act an enzyme preparation having specificity toward 1- and 3-positions theron.

According to the present invention, the enzymatic transesterification is carried out by continuously or repeatedly contacting the enzyme or the enzyme preparation having transesterification activities with a fresh supply of the dried fatty ester substrate and, whereby the intermolecular or intramolecular transesterification between the fatty acid residues proceeds in the reaction system to give the fatty ester having desired configuration and characteristics.

The term "a fresh supply of the dried fatty ester substrate" used herein means that the transesterification of the substrate has not yet been completed to the desired extent.

In some cases, it is desirable to contact, the substrate with an adsorbent before the transesterification. It is assumed that this may be due to the presence of an unknown transesterification inhibitor which may be a trace component resulting from the deterioration of the substrate. Even if the substrate has been treated with an adsorbent, the substrate sometimes inhibits the transesterification, when it is allowed to stand for a long time. Therefore, it is preferable to subject the substrate to the transesterification reaction shortly after being treated with an absorbent. Preferred examples of the adsorbent are activated clay, activated carbon, silica gel, used enzyme preparation, particularly, those containing carriers used in the present invention or the like. This treatment with an adsorbent can be carried out in a batchwise operation or can be continuously carried out by passing the substrate through a column packed with the above adsorbent before the transesterification.

The enzymatic transesterification of the present invention can be carried out in a batchwise operation or a continuous operation using, for example, a fluidized bed of the enzyme preparation or a column packed with the enzyme preparation. In view of the continuous or repeated use of the enzyme preparation, as mentioned above, it is preferable to disperse, adsorb or bond the enzyme in or to the carrier so as to readily recover the enzyme preparation.

In the continuous or repeated use of the enzyme preparation, small portions of the fresh enzyme preparation can be supplemented, while small portions of the enzyme preparation which are practically inactivated, are removed from the reaction system. By this operation, transesterification activities can be maintained for a long time and, in comparison with using the fresh enzyme preparation alone, there can be prevented an undesirable increase in the formation of hydrolyzates and deterioration and variability of quality resulted therefrom. Further, loading can be increased and the amount of the hydrolyzates formed per unit substrate or unit time is decreased by this operation.

Generally, the transesterification reaction can be carried out at 20° to 75° C., preferably, at 20° to 60° C. until the transesterification proceeds to a desired extent. When the enzyme preparation is thermal resistant, the reaction can be carried out at about 70° C. with little inactivation of the enzyme preparation.

The following Examples and Reference Examples further illustrate the present invention in detail but are not to be construed to limit the scope thereof. In the Examples, all the "parts" and "%" are by weight unless otherwise stated.

EXAMPLES 1, 2 AND 3 AND REFERENCE EXAMPLES 1, 2 AND 3

A commercially available lipase originated from *Rhizopus niveus* (300 g) was dissolved in water (750 g) at about 5° C. and the solution was slowly added to Celite 545 (diatomaceous earth produced by Johns Mansville Sales Corp., U.S.A.) (750 g) with stirring to give a paste which turned into a wet powder. The powder was divided into 5 portions and one portion was freeze-dried (temperature: $-23°$ C., degree of vacuum: 0.6 Torr) (Reference Example 2). Each of the other three portions was placed in a desiccator connected to a vacuum pump and vacuum-dried at 6 Torr for 4 hours (Reference Example 3), at 8 Torr for 20 hours (Example 1) or at 15 Torr for 4 days (Example 2) to attain the final water content of about 1.4%. During this vacuum drying, external heating and leakage of air were occasionally effected. The remaining one portion was also placed in a desiccator connected to a vacuum pump and vacuum-dried, firstly, under the same conditions as in Example 2 to attain 0.4 of degree of moisture, and then at 15 Torr for 1 day with increased external heating to attain the final water content of about 1.4% (Example 3). Lipid-degrading activities and transesterification activities of the above commercially available lipase (Reference Example 1) and the above-obtained enzyme preparation are shown in Table 2.

TABLE 2

| Enzyme Preparations | Lipolytic activities | Ka | Kr × 10³ |
|---|---|---|---|
| Reference Example 1 | 4500 | 0 | — |
| Reference Example 2 | 1250 (97.2%)* | 3.0 | 2.4 |
| Reference Example 3 | 1240 (97.3%) | 3.2 | 2.6 |
| Example 1 | 1210 (94.1%) | 12.7 | 10.5 |
| Example 2 | 1150 (89.4%) | 28.5 | 24.8 |
| Example 3 | 1200 (93.3%) | 29.7 | 24.8 |

*The percentages in the parentheses show the rate of remaining activities. The percentages are calculated based on the net amount of the lipase.

As is clear from Table 2, even if the lipase maintains its own activities, substantial Ka value is not activated unless it is dried at the adequately slow drying rate.

EXAMPLE 4

A commercially available lipase originated from *Rhizopus niveus* (1 part) was dissolved in cold water (4 parts) and the solution was thoroughly stirred. Granular diatomaceous earth (2.5 parts) was added to the solution and the mixture was slowly dried under a reduced pressure to obtain an enzyme preparation having 1.5% of water content and 25.7 of Ka value.

The enzyme preparation (8 g) was packed in a glass column (16 mm in diameter) and a mixed oil (water content: 0.015%) which was prepared by previously mixing a middle melting point fraction of palm oil (iodine value: 34.5, DG content: 2.8%) and methyl stearate (purity: 90%) at the ratio of 1:1 and dried by vacuum heat drying was passed through the column at the superficial velocity in the column of 0.06/hr. The degree of conversion and DG content are shown in Table 3.

TABLE 3

| (days) | Operating time | | | | | |
|---|---|---|---|---|---|---|
| | 1 | 2 | 5 | 8 | 10 | 12 |
| Degree of conversion* | 0.98 | 0.98 | 0.94 | 0.85 | 0.83 | 0.79 |

TABLE 3-continued

| (days) | Operating time | | | | | |
|---|---|---|---|---|---|---|
| | 1 | 2 | 5 | 8 | 10 | 12 |
| DG content (%) | 9.3 | 6.7 | 4.5 | 4.1 | 4.3 | 4.0 |

*Palmitic acid is regarded as the guide fatty acid and random distribution of fatty acid residues at 1- and 3-positions of the glyceride is regarded as "completely reacted state".

EXAMPLE 5

Ten columns as in Example 4 were connected in series and a mixed oil as in Example 4 was passed through the column at the superficial velocity in the column of 0.5/hr. On the every seventh day after the operation has been started, a newly prepared column was connected to the outlet end of the columns and the column assembled to the inlet side of the columns was removed. From about 2 months after the operation has been started, the composition of the oil passed through the columns become constant. After removal of the methyl ester, the oil had the following composition:

Fatty acids composition: $C_{14}$ 0.4; $C_{16}$ 26.3; $C_{17}$ 6.2; $C_{18}$ 39.4; $C_{18:1}$ 30.9; $C_{18:2}$ 2.4; $C_{20}$ 0.3

DG content: 4.1%

When this oil was subjected to solvent fractionation at 6° C. to remove solid therein, an oil quite similar to cacao butter was obtained. This oil was readily subjected to a tempering operation and could compare with cacao butter.

REFERENCE EXAMPLE 4

When the same procedure was repeated as described in Example 5 except that 0.3% of water was added to the oil to be passed through the columns, the resulting oil contained 13% of DG.

EXAMPLE 6

Coconut oil (100 parts) and olive oil (100 parts) were mixed and dried by vacuum heat drying. The resulting mixed oil contained 2.1% of DG and 0.014% of moisture.

A commercially available lipase originated from *Rhizopus niveus* (1 part) was dissolved in cold water (4 parts) and the solution was thoroughly stirred. Perlite powder (2.5 parts) was admixed with the solution and the mixture was slowly dried at 25° C. under a reduced pressure to give an enzyme preparation having 2.0% of water content and 20 of Ka valued.

The enzyme preparation (10 parts) was added the above-obtained mixed oil and the reaction was carried out with stirring at 40° C. for 3 days under the conditions for preventing moisture absorption.

After completion of the reaction, the enzyme preparation was recovered from the reaction system and, according to the same procedure, the recovered enzyme preparation was again reacted with a fresh supply of the mixed oil for 3 days. This procedure was further repeated twice, but the third run was for 4 days and the fourth run was for 5 days. After completion of the reaction, the DG content of each run was 4.5%, 3.1%, 2.9% or 2.8% in order.

EXAMPLE 7 AND REFERENCE EXAMPLES 5 AND 6

According to the same procedures as is described in Example 2 and Reference Example 2, enzyme preparations were prepared by using a commercially available lipase originated from *Rhizopus japonicus* and perlite as the carrier. Lipid-degrading activities and transesterification activities of the above commercially available lipase (Reference Example 5) and the above-obtained enzyme preparations (Reference Example 6 and Example 7) are shown in Table 4.

TABLE 4

| Enzyme Preparations | Lipolytic activities | Ka | Kr × $10^3$ |
|---|---|---|---|
| Reference Example 5 | 1600 | 12.0 | 7.5 |
| Reference Example 6 (freeze-dried) | 455 (99.6%)* | 4.4 | 9.7 |
| Example 7 | 450 (98.5%) | 7.1 | 15.8 |

*See Table 2.

As is clear from Table 4, although the commercially available lipase has transesterification activities, the Kr value is remarkably increased by the treatment of the present invention.

Equal amounts of a middle melting point fraction of palm oil (iodine value: 33.2) and methyl stearate (partially containing $C_{16}$ fatty ester) was mixed and dried by vacuum heat drying to give a substrate having 0.015% of water content.

The substrate (200 g) and the commercially available lipase (Reference Example 5, 5.62 g) or the enzyme preparation (Example 7, 20 g) were placed in a 500 ml flask and reacted at 40° C. with stirring (200 r.p.m.) to attain 0.9 of degree of conversion (palmitic acid was regarded as the guide fatty acid and random distribution of fatty acid residues at 1- and 3-positions of the gliceride regarded as "completely reacted state"). After completion of the reaction, the enzyme or the enzyme preparation was separated from the reaction mixture and recovered. The same procedure was repeated by using the recovered enzyme or enzyme preparation and a fresh supply of the substrate to attain 0.9 of degree of conversion. The number of days necessary to attain 0.9 of degree of conversion in each run is shown in Table 5.

TABLE 5

| Enzyme | 1st run | 2nd run | 3rd run | 7th run | 9th run |
|---|---|---|---|---|---|
| Reference Example 5 | 6 | 7 | 9 | — | — |
| Example 7 | 3 | 3 | 4 | 6 | 10 |

As is clear from Table 5, transesterification activities of the enzyme preparation of Example 7 is much higher than that of Reference Example 5 in each run and the enzyme preparation treated by the method of the present invention is sufficiently fit for repeated use.

EXAMPLE 8

When the same procedure was repeated by using the lipase of Reference Example 5 and a middle melting point fraction of palm oil containing 4.2% of DG, the DG content of the 1st to 3rd runs were 7.2%, 5.5% and 5.6%, respectively.

EXAMPLE 9

A commercially available lipase originated from *Rhizopus niveus* (300 g, Kr=0.0) was dissolved in cold water at about 5° C. (1200 ml) and the solution was incorporated in granular diatomaceous earth (750 g). The mixture was slowly stirred so that the carrier was not destroyed and dried for 6 days under a pressure of 15 Torr to obtain an enzyme preparation having 1.3% of water content (Ka=27.5, Kr=0.022).

According to the method of determination of transesterification activities as described hereinbefore, a substrate prepared by mixing equal amounts of coconut oil and methyl stearate was transesterified by using the above-obtained enzyme preparation (1 g). Change of the fatty acids composition of the resulting oil with time is shown in Table 6.

TABLE 6

| Carbon number of fatty acids | t (day) | | | | | | |
|---|---|---|---|---|---|---|---|
| | 0/24 | 6/24 | 12/24 | 24/24 | 2 | 4 | 8 |
| 8 | 0 | 0.7 | 1.4 | 2.6 | 3.0 | 3.9 | 4.4 |
| 10 | 0 | 0.5 | 0.8 | 1.6 | 2.2 | 3.0 | 3.2 |
| 12 | 0 | 2.7 | 4.6 | 7.5 | 10.6 | 12.9 | 12.9 |
| 14 | 0.2 | 1.9 | 3.2 | 5.0 | 7.3 | 8.4 | 8.5 |
| 16 | 10.0 | 10.4 | 10.3 | 10.8 | 11.2 | 11.7 | 11.3 |
| 16–18 | 0.3 | 0.6 | 0.5 | 0.4 | 0.4 | 0.4 | 0.4 |
| 18:0 | 89.0 | 82.7 | 78.9 | 71.4 | 64.8 | 59.1 | 56.4 |
| 18:1 | | | | | | | 2.3 |
| 18:2 | — | — | — | 0.1 | 0.2 | 0.3 | 0.7 |
| 20:0 | 0.5 | 0.4 | 0.3 | 0.3 | 0.3 | 0.3 | 0.4 |
| 100 x | 0 | 21.1 | 35.9 | 58.7 | 82.8 | 100 | 100 |
| $\ln \frac{1}{1-x}$ | 0 | 0.237 | 0.445 | 0.880 | 1.760 | — | — |

Since the amount of the target fatty acid ($C_{12}$) was not increased after $t=4$, x and $$\ln \frac{1}{1-x}$$

were calculated by taking a and c as 0.128 and 0, respectively.

It is adequate to determine the activities by regarding the reaction as a first-order reaction since the relationship between t and $$\ln \frac{1}{1-x}$$

is almost linear.

EXAMPLE 10

Polyvinyl alcohol (2 g) was cyanogenated with cyanogen bromide and washed with water. 0.1 M phosphate buffer (pH 7.5) (50 ml) and a commercially available pancreas lipase (5 g) were added to the above cyanogenated polyvinyl alcohol and the mixture was stirred at 5° C. overnight, filtered and dried under a reduced pressure to give an enzyme preparation (water content: 2.1%).

A mixture of equal amounts of olive oil and ethyl stearate was passed through a silica gel column and slowly dried by vacuum heat drying to give a substrate (water content: 0.01%).

The above-prepared enzyme preparation (1.5 parts) was added to the substrate (20 parts) and the mixture was reacted at 40° C. When the degree of conversion was reached to 0.8, the enzyme was separated from the reaction mixture and recovered. The degree of conversion was determined by regarding oleic acid as the target fatty acid. The same procedure was repeated by using the recovered enzyme preparation and a fresh supply of the substrate. DG content of the resulting oil in each run is shown in Table 7.

TABLE 7

| | 1st run | 2nd run | 3rd run | 4th run |
|---|---|---|---|---|
| Reaction time (day) | 4 | 5 | 6 | 6 |
| DG content (%) | 7.8 | 3.5 | 3.0 | 3.2 |

EXAMPLE 11

A commercially available lipase originated from *Rhizopus delemar* (1 part) was dispersed in cold water (4 parts). Kaolinite (2.5 parts) was added to the dispersion and the mixture was dried at a slow initial drying rate in air flow at 20° C. to give an enzyme preparation.

A mixed oil of equal amount of olive oil and coconut oil was divided into two portions. Clay (white earth) was added to the one portion of the mixed oil in the concentration of 2%. After stirring, the resulting mixture was dried by vacuum heat drying and clay was removed from the mixture. The other portion of the mixed oil was directly dried by vacuum heat drying. Both the resulting substrates contained 0.01% of water and 27% of triglyceride having 54 carbon atoms.

The above-prepared enzyme preparation was added to each substrate and the mixture was reacted with stirring at 40° C. When the content of the glyceride having 54 carbon atoms was decreased to 10% or less, the enzyme preparation was recovered from the reaction mixture and the same procedure was repeated by using the recovered enzyme preparation and a fresh supply of the substrate. The DG content of the resulting oil in each run is shown in Table 8.

TABLE 8

| | | 1st run | 2nd run | 3rd run | 4th run |
|---|---|---|---|---|---|
| Enzyme without clay treatment | reaction time (day) | 3 | 3 | 4 | 6 |
| | DG content (%) | 7.0 | 4.2 | 3.8 | 3.9 |
| Enzyme with clay treatment | reaction time (day) | 2 | 2 | 3 | 3 |
| | DG content (%) | 7.2 | 4.0 | 3.6 | 3.8 |

EXAMPLE 12

A commercially available pancreas lipase (1.5 parts) was dissolved in cold water (5 parts) and granular perlite (4 parts) was added to the solution. The mixture was dried at 15° C. under a reduced pressure to give an enzyme preparation (water content: 2%).

A mixture of equal amounts of propylene glycol dioleate and ethyl palmitate was dried by vacuum heat drying to give a substrate (water content: 0.01%).

The above prepared enzyme preparation was packed in a column and, according to the same procedure as in Example 5, the enzymatic transesterification was carried out by using the substrate. After removal of fatty esters from the resulting oil, the propylene glycol ester having a lower content of mono-ester and a higher content of palmitic acid was obtained.

EXAMPLE 13

Activated clay (3 parts) was mixed with methyl laurate (30 parts) and egg yolk lecithin (50 parts) and the mixture was dried by vacuum heat drying to give a substrate (water content: 0.01%).

By using the substrate, the same procedure as is described in Example 12 was repeated to obtain a lauric acid-introduced lecithin.

EXAMPLE 14

Ten columns as in Example 4 were arranged in a row and the same substrate as in Example 4 (1500 g) placed in a storage tank was uniformly circulated through the each column from the bottom to the top. When the oldest column of all ten columns was replaced with a newly prepared column, the substrate was also replaced with a fresh supply thereof on the every sixth day after the operation has been started, the fatty acids composition of the resulting oil was stable after removal of methyl esters.

EXAMPLE 15

The same procedure as is described in Example 6 was repeated except that an enzyme preparation originated from *Candida cylindracae* (Ka=17.8) and a mixture prepared by mixing equal amounts of olive oil and oleic acid was substituted for the enzyme preparation and the substrate, DG content of each run was 5.9% (after reaction for 3 days), 3.8% (after reaction for 3 days), 3.5% (after reaction for 4 days) or 3.2% (after reaction for 5 days).

EXAMPLE 16

The same procedure as is described in Example 6 was repeated except that the substrate was prepared by mixing a mixture of equal amount of safflower oil and stearic acid (DG content: 1.2%, water content: 0.009%) with hexane (300 parts) and 20 parts of the enzyme preparation was used. After removal of hexane and fatty acids from the reaction mixture, the DG content of each run was 6.8% (after reaction for 3 days), 5.1% (after reaction for 3 days), 4.7% (after reaction for 4 days) or 4.3% (after reaction for 5 days).

What is claimed is:

1. A method for preparing an enzyme preparation which comprises dispersing, adsorbing or bonding an enzyme having lipolytic activities in or to a carrier in an aqueous system and drying the resulting mixture at a drying rate and to a moisture level sufficient to activate or increase Kr of the enzyme, wherein Kr is the relative transesterification activity value of the enzyme determined by dividing the absolute transesterification activity Ka by the lipolytic activities of the enzyme according to the following formula:

$$Ka = \frac{S}{E} \times \frac{1}{t} \ln \frac{1}{1-x}$$

in which
S is the amount of a substrate used in a transesterification reaction for the determination of Ka;
E is the amount of the enzyme used in the reaction;
t is the reaction time expressed in terms of days;
x is the degree of conversion in the reaction; and
the lipolytic activities is the micromolar amount of fatty acids formed per 1 minute by 1 g of the enzyme.

2. A method according to claim 1, wherein activation or increase in Kr value is 0.005 or more.

3. A method according to claim 1, wherein the carrier is a member selected from the group consisting of diatomaceous earth, kaolinite, perlite, silica gel, cellulose powder, polyvinyl alcohol and calcium carbonate.

4. A dried lipase preparation having a Kr value of 0.01 or more.

5. A method according to claim 1 wherein the drying is effected by vacuum drying.

6. A method according to claim 2 wherein the drying is effected by vacuum drying.

7. A method according to claim 1 wherein the drying is effected by pneumatic drying.

8. A method according to claim 2 wherein the drying is effected by pneumatic drying.

9. A method according to claim 1 wherein the drying rate is such that the decrease in the degree of moisture is at most 0.3 per hour, wherein said degree of moisture represents the ratio of the weight of water in the mixture to the dry weight of the mixture in which said dry weight represents 1.

10. A method according to claim 1 in which the weight ratio of the enzyme to carrier is between about 2:1 to 1:20.

11. A dried lipase produced by the method of claim 1.

* * * * *